United States Patent [19]
Doi et al.

[11] Patent Number: 6,041,096
[45] Date of Patent: Mar. 21, 2000

[54] METHOD AND APPARATUS FOR TOTAL REFLECTION X-RAY FLUORESCENCE SPECTROSCOPY

[75] Inventors: Ichiro Doi; Shoichiro Tonomura, both of Nobeoka, Japan

[73] Assignee: Asahi Kasei Kogyo Kabushiki Kaisha, Osaka, Japan

[21] Appl. No.: 09/011,046

[22] PCT Filed: Aug. 2, 1996

[86] PCT No.: PCT/JP96/02185

§ 371 Date: Feb. 6, 1998

§ 102(e) Date: Feb. 6, 1998

[87] PCT Pub. No.: WO97/06430

PCT Pub. Date: Feb. 20, 1997

[30] Foreign Application Priority Data

Aug. 9, 1995 [JP] Japan .................................... 7-203393

[51] Int. Cl.[7] .................................................. G01N 23/223
[52] U.S. Cl. ............................................. 378/48; 378/45
[58] Field of Search ................................. 378/44, 45, 46, 378/48, 49

[56] References Cited

U.S. PATENT DOCUMENTS

| | | |
|---|---|---|
| 4,573,181 | 2/1986 | Grönberg et al. . |
| 5,246,216 | 9/1993 | Ohsugi et al. ............................. 378/46 |
| 5,457,726 | 10/1995 | Miyazaki .................................. 378/45 |
| 5,497,407 | 3/1996 | Komatsu et al. . |

FOREIGN PATENT DOCUMENTS

| | | | |
|---|---|---|---|
| 004244242 | 6/1994 | Germany ................................ 378/46 |
| 58-171653 | 10/1983 | Japan . |
| 59-214743 | 12/1984 | Japan . |
| 2-10639 | 1/1990 | Japan . |
| 4-305150 | 10/1992 | Japan . |
| 405240808 | 9/1993 | Japan ...................................... 378/46 |
| 7-167804 | 7/1995 | Japan . |

*Primary Examiner*—David P. Porta
*Attorney, Agent, or Firm*—Finnegan, Henderson, Farabow, Garrett & Dunner, L.L.P.

[57] ABSTRACT

A method and an apparatus for total reflection X-ray fluorescence spectroscopy which facilitates total reflection X-ray fluorescent spectroscopy of a sample having irregularities. Primary X-rays are emitted to a standard sample having a smooth surface at a plurality of irradiation angles, a characteristic X-ray spectrum is measured at each of irradiation angles, a characteristic X-ray intensity and a scattered X-ray intensity are determined therefrom, a calibration coefficient is determined in the form of a function of the scattered X-ray intensity by dividing a know quantity of an analyzed element of the standard sample by the determined characteristic X-ray intensity, a characteristic X-ray spectrum when a measured sample having irregularities on the surface is irradiated with primary X-rays at a reference irradiation angle smaller than a critical total reflection angle is measured a characteristic X-ray intensity and a scattered X-ray intensity for the analyzed element are determined therefrom, a calibration coefficient to be applied to the measured sample is determined on the basis of the determined scattered X-ray intensity, and the quantity of the analyzed element is calculated by multiplying the calibration coefficient with the characteristic X-ray intensity for the analyzed element.

4 Claims, 8 Drawing Sheets

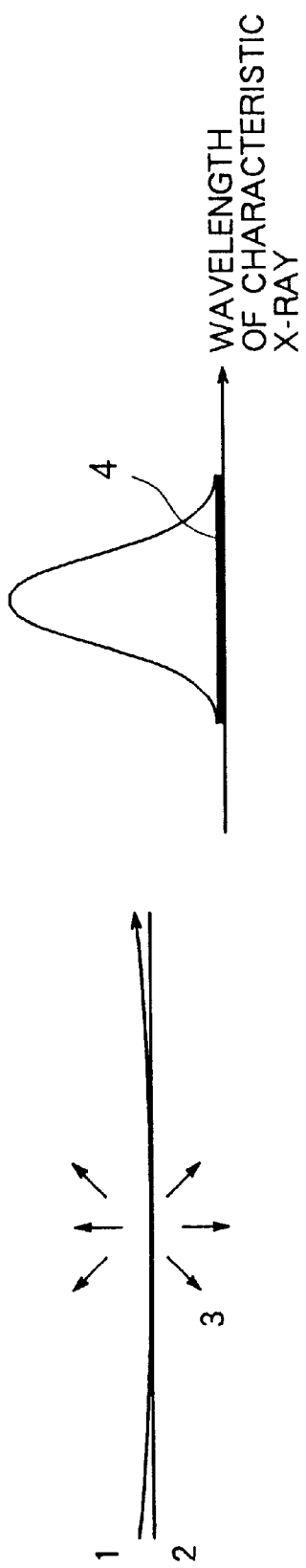

METHOD AND APPARATUS FOR TOTAL REFLECTION X-RAY FLUORESCENCE SPECTROSCOPY

TECHNICAL FIELD

The present invention concerns a method and an apparatus for total reflection X-ray spectroscopy for conducting analysis by measuring characteristic X-rays emitted from a measured sample when the measured sample is irradiated with primary X-rays at a small angle near a critical total reflection angle.

BACKGROUND ART

The method for total reflection X-ray spectroscopy is adapted for irradiating primary X-rays to a measured sample, by which an element present in the measured sample emits secondary X-rays referred to as characteristic X-rays, and conducting elemental analysis for the sample by using the characteristic X-ray, and this has been known long seen.

Since the wavelength of the characteristic X-rays is inherent to the element which is present, an element present in the sample can be analyzed qualitatively based on the wavelength of each of characteristic X-rays appearing in the characteristic X-rays of the measured sample. Further, since each characteristic X-ray intensity reflects the existing quantity of the element, it is also possible to recognize the existing quantity of the element based on the analysis of the characteristic X-ray spectrum. In this case, it is generally required that a standard sample having a known quantity of an analyzed element is provided and a relation between the quantity and the characteristic X-ray intensity is determined previously.

What should be noted in the method for X-ray fluorescence spectroscopy is that not only the characteristic X-rays appears in the characteristic X-ray spectrum for the sample irradiated with primary X-rays but also scattered X-rays scattered in the inside of the sample is also included, and the scattered X-ray intensity constitutes a major factor for determining a detection limit of the X-ray fluorescence spectroscopy. That is, if the element present in the sample emits characteristic X-rays only at an intensity equal with or lower than the fluctuation of the scattered X-rays, the element can not be analyzed quantitatively.

By the way, while the X-ray fluorescence spectroscopy is applicable also to the analysis of microelements localized only at the surface of a semiconductor or the like, a problem due to scattered X-rays is caused in this case. That is, since the analyzed element is present only on the surface of the sample, the characteristic X-rays thereof are also emitted only from the surface, whereas scattered X-rays are emitted also from the inside of the sample. Accordingly, for the intensity of both of them, the latter is outstandingly great and no sufficient detection limit can be obtained.

As an analyzing method for overcoming the problem, it has been known total reflection X-ray fluorescence spectroscopy of irradiating primary X-rays to a sample at a smaller angle than a critical total reflection angle and conducting elemental analysis for the surface of the sample by using the characteristic X-rays excited therewith. In this total reflection X-ray fluorescence spectroscopy, the intruding depth of the primary X-rays into the sample is extremely shallow and it is considered to be an order of several nm, for example, in single crystals of silicon. Therefore, the scattered X-ray intensity emitted in the sample is reduced greatly, and an analyzed element present only on the surface of the sample can be analyzed at a low detection limit. The feature of the method for total reflection X-ray fluorescence spectroscopy, as can be seen from the principle thereof, resides in that the characteristic X-rays for the analyzed element on the surface of the sample are excited substantially only by the primary X-rays.

For obtaining an analysis value by the total reflection X-ray fluorescence spectroscopy, calibration with a standard sample is required like that in the case of a usual X-ray fluorescence spectroscopy. In the case of the total reflection X-ray fluorescence spectroscopy, since the object is measurement, particularly, for the quantity of the analyzed element on the surface of the sample calibration is conducted by using a standard sample having a known quantity of the analyzed element on the surface. In the present specification, the characteristic X-ray intensity for the known quantity of the analyzed element determined by using a standard sample is hereinafter referred to as a calibration coefficient.

However, the existent total reflection X-ray fluorescence spectroscopy described above involves a not yet solved subject as described below.

That is, while it is required to irradiate the primary X-rays at an angle smaller than a critical total reflection angle to the sample in the total reflection X-ray fluorescence spectroscopy in view of the principle thereof, it is pre-conditioned that the sample surface is an ideal smooth surface.

For instance, a silicon wafer can be regarded as an ideal smooth surface so long as it is within a range of a beam diameter of X-rays employed usually. However, the object for the analysis of the total reflection X-ray fluorescent spectroscopy is not always restricted to a sample having such an ideal smooth surface.

Many thin film samples, for example, of polysilicon often have irregularities about from several tens to several hundreds nm. If such irregularities are present on the surface, even when primary X-rays are irradiated at an angle smaller than the critical total reflection angle to an averaged sample surface (for example, an envelope plane for the irregularities on the surface), there is present a portion irradiated with an angle greater than the critical total reflection angle when observed locally, and primary X-rays intrude into the sample through such a portion to increase the scattered X-ray intensity.

As a result, an undesired situation as described below will be caused in the total reflection X-ray fluorescence spectroscopy for a sample having irregularities. That is, assuming that a standard sample for obtaining an analysis value has a substantially ideal smooth surface, even when the standard sample and the measured sample are analyzed under identical conditions, the intensity of the scattered X-rays emitted from the inside of the sample is much more greater in the later.

Therefore, the characteristic X-rays from the analyzed element present on the surface of the measured sample are excited not only by the primary X-rays but excited also by the scattered X-rays from the inside of the sample. Accordingly, no accurate analysis value can be obtained if calibration is conducted by using the characteristic X-ray intensity for the standard sample, as it is, for which scattered X-rays from the inside of the sample is negligible substantially.

For avoiding such a situation, it may be considered to prepare a standard sample itself with a sample having the same irregularities as those of the measured sample. However, this method involves the following not yet solved subjects.

At first, it is difficult to form identical irregularities both for the standard sample and the measured sample. Identical irregularity means here that the scattered X-ray intensity caused by the irregularities are identical. That is, irregularities for both of them can not be equal unless a standard sample emitting scattered X-days identical with those of the measured sample and it is generally difficult to prepare such a standard sample.

Secondly, in a case of analyzing samples having various irregularities, preparation of standard samples corresponding to respective irregularities requires an operation of depositing a known quantity of an analyzed element to the surface of standard sample and calibration to determine whether the quantity of the analyzed element is surely equal with a predetermined quantity, which is time and cost consuming.

DISCLOSURE OF THE INVENTION

The present invention has been accomplished while taking notice of the not yet solved subjects in the prior art described above and it is an object thereof to provide a method and an apparatus for total reflection X-ray fluorescence spectroscopy capable of analyzing a substance to be analyzed easily and accurately, without forming irregularities in accordance with a measured sample, an operation of depositing a known quantity of an analyzed element and calibration.

For attaining the foregoing object, the invention provides an apparatus for total reflection X-ray fluorescence spectroscopy of irradiating primary X-rays to a measured sample at an angle near a critical total reflection angle, and measuring a characteristic X-ray spectrum emitted from the measured sample by the primary X-rays thereby analyzing an analyzed element on the measured sample, the apparatus comprising an X-ray intensity measuring means for a standard sample of irradiating primary X-rays previously on a standard sample having substantially the same composition as that of a measured sample and having a smooth surface at a plurality of irradiation angles near a total reflection angle and determining a characteristic X-ray intensity for an analyzed element and a scattered X-ray intensity at a wavelength of the characteristic X-rays for the analyzed element, a function memory means of determining a calibration coefficient indicative of a relation between the characteristic X-ray intensity determined by the X-ray intensity measuring means for the standard sample and a known quantity of the analyzed element on the basis of both of them as a function of the scattered X-ray intensity and storing the function, an X-ray intensity measuring means for a measured sample of measuring a characteristic X-ray spectrum when the primary X-rays are irradiated to the measured sample at an angle smaller than a critical total reflection angle and determining a characteristic X-ray intensity for the analyzed element appearing in the characteristic X-ray spectrum and a scattered X-ray intensity at a wavelength of the characteristic X-rays for the analyzed element, a calibration coefficient calculation means for determining a calibration coefficient by substituting the scattered X-ray intensity determined by the X-ray intensity measuring means for the measured sample as the scattered X-ray intensity of the function stored in the function memory means, and a calculation means for the quantity of the analyzed element by calibrating the characteristic X-ray intensity for the analyzed element determined by the calibration coefficient calculation means and calculating the quantity of the analyzed element.

Further, the invention has a feature wherein the function memory means stores the relation between the scattered X-rays intensity and the calibration coefficient as a functional equation.

Further, the invention has a feature wherein the function memory means stores the relation between the scattered X-ray intensity and the calibration coefficient as a control map.

Furthermore, the invention provides a method for total reflection X-ray fluorescence spectroscopy of irradiating primary X-rays to an analyzed substance on a measured sample at an angle near a critical total reflection angle, measuring a characteristic X-ray spectrum and a scattered X-ray spectrum emitted by the primary X-ray from the measured sample thereby analyzing the analyzed substance on the measured sample, comprising a first step of irradiating primary X-rays previously on a standard sample having substantially the same composition as that of a measured sample and having a smooth surface at a plurality of irradiation angles near a total reflection angle and measuring the characteristic X-ray spectrum, a second step of calculating the characteristic X-ray intensity for the analyzed element and the scattered X-ray intensity at the wavelength of the characteristic X-rays for the analyzed element by using the measured characteristic X-ray spectrum and determining a calibration coefficient indicative of a relationship between the calculated characteristic X-ray intensity and a known quantity of the analyzed element on the basis of both of them as a function of the scattered X-ray intensity, a third step of measuring the characteristic X-ray spectrum when primary X-rays are irradiated to a measured sample at an angle smaller than a critical total reflection angle and determining a characteristic X-ray intensity for the analyzed element appearing in the characteristic X-ray spectrum and a scattered X-ray intensity at a wavelength of the characteristic X-rays for the analyzed element, a fourth step of applying the scattered X-ray intensity for the analyzed element determined in the third step to the function of the calibration coefficient in the second step and determining a calibration coefficient to be applied to the measured sample and a fifth step of multiplying the characteristic X-ray intensity for the analyzed element determined in the third step with the calibration coefficient determined in the fourth step to calculate the quantity of the analyzed element.

In a case of a sample having irregularities, since the scattered X-rays are emitted due to the presence of the irregularities even when primary X-rays are irradiated to a sample at an irradiation angle smaller than the critical total reflection angle in view of average, it is not appropriate to be referred to as the total reflection X-ray fluorescence spectroscopy in a strict meaning. However, since it is identical with the existent total reflection X-rays fluorescence spectroscopy in that it is intended to reduce the scattered X-ray by irradiation of primary X-rays at a small angle thereby improving the detection limit and in that analysis is conducted by utilizing the characteristic X-rays from the analyzed element, the total reflection X-ray fluorescence spectroscopy applied to a sample having irregularity is also referred to under the identical name in this specification.

Details for the present invention will be explained below.

The reason why total reflection X-ray fluorescence spectroscopy is possible to an analyzed sample having irregularities by using a standard sample having a smooth surface is as described below.

That is, for the primary X-rays and emitting situation of scattered X-rays and qualitative characteristic X-ray spectrum on the surface of a sample upon analysis of the sample by the total reflection X-ray fluorescence spectroscopy, scattered X-rays 3 are scarcely emitted when primary X-rays 2 are irradiated on a sample surface 1 as shown in FIG. 4(a), in a case of an ideal smooth surface with no irregularities on the sample surface, and characteristic X-rays due to an analyzed element on sample surface are excited substantially only by the primary X-ray with the scattered X-rays intensity 4 being extremely small as shown in FIG. 4(b).

On the other hand, if irregularities are present on the sample surface, if primary X-rays 2 are irradiated at the same irradiation angle as that in FIG. 4(a) to an envelope plane for the irregularities on the sample surface 1, since irradiated primary X-rays intrude through the irregular portion of the sample into the inside of the sample, as shown in FIG. 5(a), scattered X-rays are emitted and a portion thereof excites the characteristic X-rays due to the analyzed element on the sample surface, so that the scattered X-ray intensity 4 is increased as shown in FIG. 5(b).

By the way, when primary X-rays are irradiated to a sample having a known quantity of a standard element on the surface and having a substantially smooth surface at a plurality of irradiation angle near the critical total reflection angle, the primary X-rays and the emission situation of the scattered X-rays on the sample surface are as shown in FIG. 6(a) in which scattered X-rays 3 are scarcely emitted if the irradiation angle of the primary X-rays is sufficiently smaller than the critical total reflection angle, and the characteristic X-rays due to the analyzed element are excited substantially only by the primary X-rays with the scattered X-ray intensity 4 being extremely small as shown in FIG. 6(b).

Further, in a case where the irradiation angle of the primary X-rays is slightly greater than the critical total reflection angle as shown in FIG. 7(a), scattered X-rays 3 emitted are also increased and, correspondingly, in emitted scattered X-ray intensity 3 is increased for the characteristic X-ray intensity due to the analyzed element as shown in FIG. 7(b).

Further, in a case if the irradiation angle of the primary X-rays is sufficiently greater than the critical total reflection angle as shown in FIG. 8(a), the scattered X-rays 3 emitted are further increased and, correspondingly, the scattered X-ray intensity is further increased in the characteristic X-rays due to the analyzed element as shown in FIG. 8(b).

As described above, as the irradiation angle of the primary X-rays is increased, the intensity of the emitted scattered X-rays is increased and, correspondingly, the characteristic X-ray intensity emitted from the analyzed element present on the sample surface is also increased.

Accordingly, if a sample in which the quantity of the analyzed element present on the surface is known is used as the sample, even if a sample with no irregularities on the surface is used, it can be used as a standard sample for the calibration in the analysis of a measured sample having irregularities on the surface, by increasing the intensity of scattered X-rays emitted from the inside of the sample by varying the irradiation angle of the primary X-rays.

That is, when a calibration coefficient is determined based on a relation between the existing quantity of the analyzed element and the intensity of the characteristic X-rays so as to emit the scattered X-rays at an identical intensity with that of a measured sample having irregularities on the surface, by varying the irradiation angle of the primary X-rays relative to the sample, the existing quantity of the analyzed element can be determined by calibrating the characteristic X-ray intensity for the analyzed element determined from the characteristic X-ray spectrum for the measured sample with the calibration coefficient.

It is necessary for an apparatus for total reflection X-ray fluorescent spectroscopy for conducting such analysis to comprise an X-ray intensity measuring means for a standard sample of irradiating primary X-rays previously on a standard sample having substantially the same composition as that of a measured sample and having a smooth surface at a plurality of irradiation angles near a total reflection angle to measure a characteristic X-ray spectrum and calculating a characteristic X-ray intensity for an analyzed element and a scattered X-ray intensity at a wavelength thereof a function memory means of determining a calibration coefficient indicative of a relation between the characteristic X-ray intensity and a known quantity of the analyzed element on the basis of both of them as a function of the scattered X-ray intensity and storing the function, an X-ray intensity measuring means for a measured sample of measuring a characteristic X-ray spectrum when the primary X-rays are irradiated to the measured sample at an angle smaller than a critical total reflection angle and determining a characteristic X-ray intensity for the analyzed element appearing in the characteristic X-ray spectrum and a scattered X-ray intensity in the characteristic X-rays for the analyzed element, a calibration coefficient calculation means for determining a calibration coefficient by substituting the scattered X-ray intensity as the scattered X-ray intensity of the function and a calculation means for the quantity of the analyzed element of calibrating the characteristic X-ray intensity for the analyzed element determined by the X-ray intensity measuring means for the measured sample and calculating the quantity of the analyzed element.

An X-ray intensity measuring device may be used in common for the standard sample X-ray intensity measuring means and the measured sample X-ray intensity measuring means.

Further, since the standard sample is used for determining the calibration coefficient of the analyzed element, it is also necessary to have the analyzed element and, further, it is preferred to have a composition as close as that of the measured sample in view of the measuring accuracy.

According to the present invention, it provides an effect capable of easily and accurately analyzing the measured sample upon conducting total reflection X-ray fluorescence spectroscopy for a measured sample having irregularities on the surface, without forming irregularities in accordance with the measured sample, conducting operation of depositing a known quantity of the analyzed element and calibration.

Further, storage of a relation between the intensity of scattered X-rays and the calibration coefficient as a functional equation by the function memory means provides an effect capable of storing with a small memory capacity and easily calculating the calibration coefficient by the calibration coefficient calculation means.

Further, storage of the relation between the scattered X-ray intensity and the calibration coefficient as the control map by the function memory means provides an effect capable of calculating the calibration coefficient on the basis of the scattered X-ray intensity without conducting operation.

BRIEF EXPLANATION FOR THE DRAWINGS

Figure 4A:
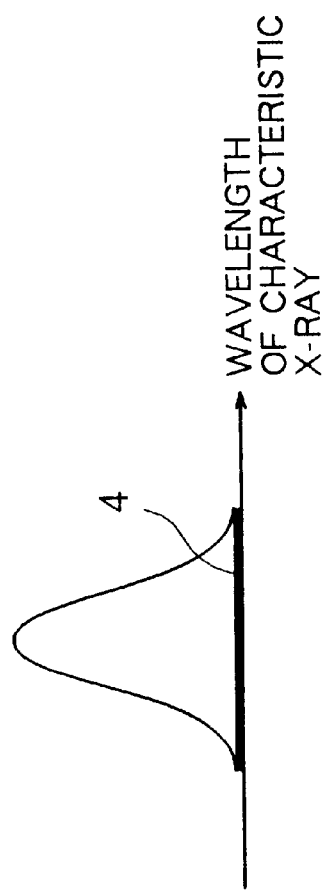
Figure 4B:
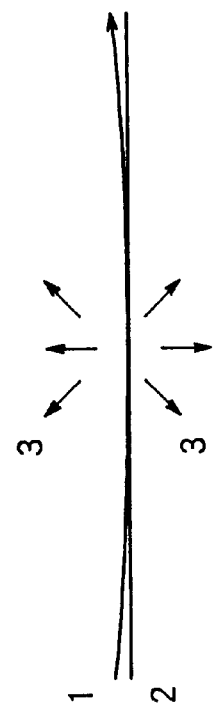

FIGS. 4(a) and 4(b) are explanatory views illustrating an emission situation of scattered X-rays and characteristic X-ray spectrum when primary X-rays are irradiated on a smooth surface of a sample.

Figures 5A, 5B:
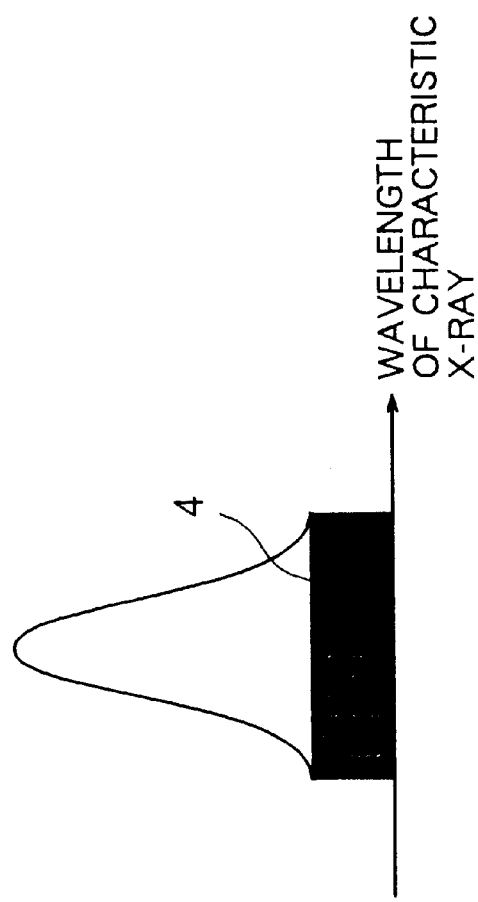

FIGS. 5(a) and 5(b) are explanatory views illustrating an emission situation of scattered X-rays and characteristic X-ray spectrum when primary X-rays are irradiated to a surface of a sample having irregularities on the surface.

FIGS. 6(a) and 6(b) are explanatory views illustrating an emission situation of scattered X-rays and characteristic X-ray spectrum when primary X-rays are irradiated to a standard sample at an angle smaller than a critical total reflection angle.

Figure 7B:
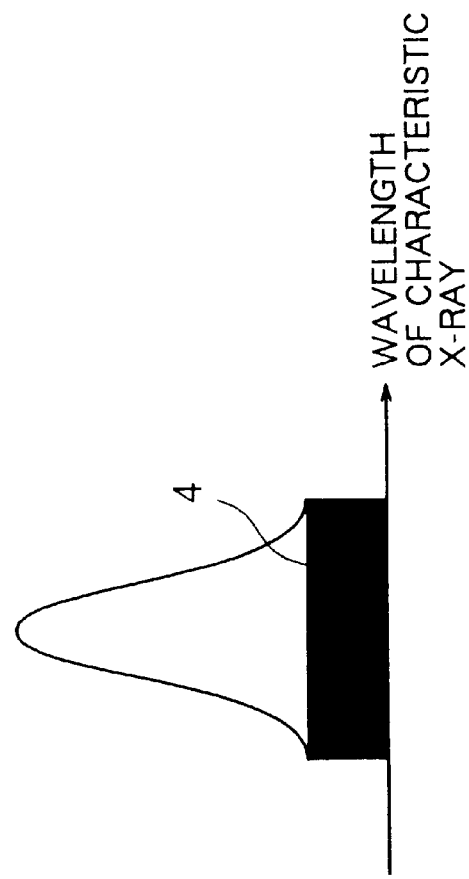
Figure 7A:
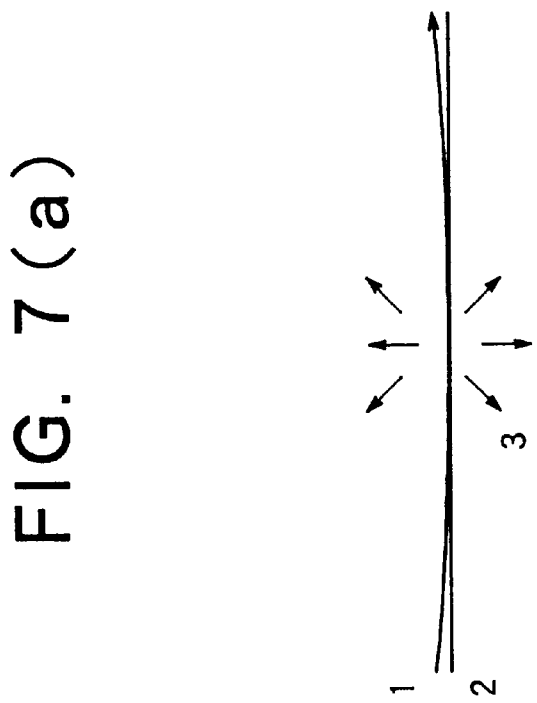

FIGS. 7(a) and 7(b) are explanatory views illustrating an emission situation of scattered X-rays and characteristic X-ray spectrum when primary X-rays are irradiated to a standard sample at an angle near a critical total reflection angle.

Figures 8A, 8B:
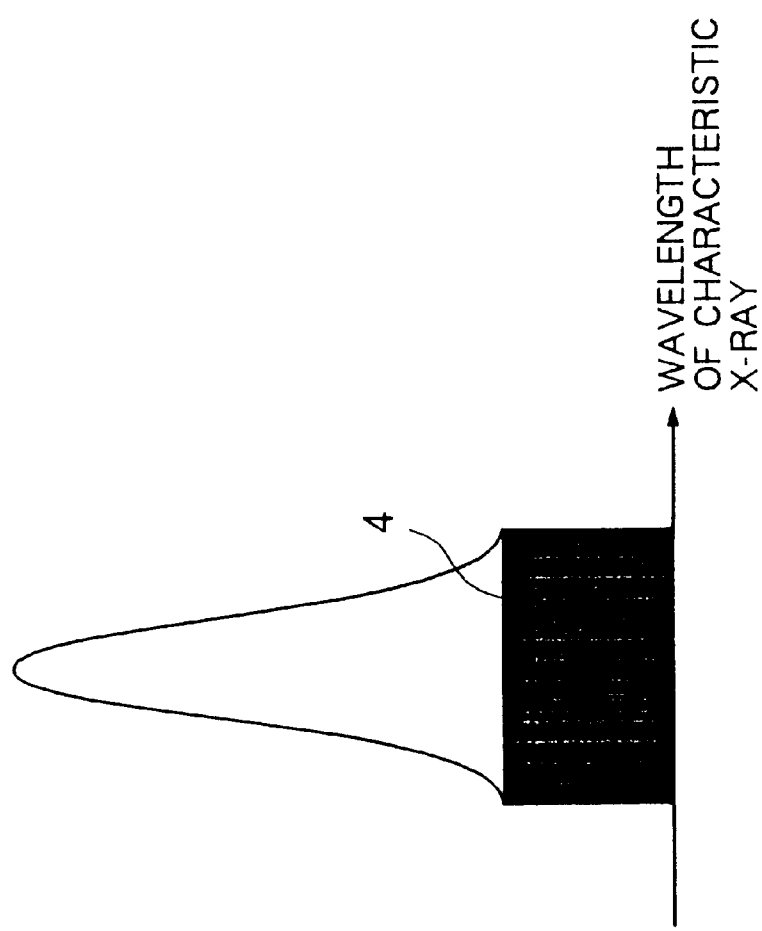

FIGS. 8(a) and 8(b) are explanatory views illustrating an emission situation of scattered X-rays and characteristic X-ray spectrum when primary X-rays are irradiated to a standard sample at an angle greater than a critical total reflection angle.

EXPLANATION FOR REFERENCES

11 . . . primary X-ray source
12 . . . placing bed
13 . . . measured sample
14 . . . standard sample
15 . . . semiconductor detector
16 . . . operation processing device
16 . . . height adjusting mechanism
17 . . . angle adjusting mechanism Best Mode for Practicing the Invention An embodiment of the present invention is explained with reference to the drawings.

Figure 1:
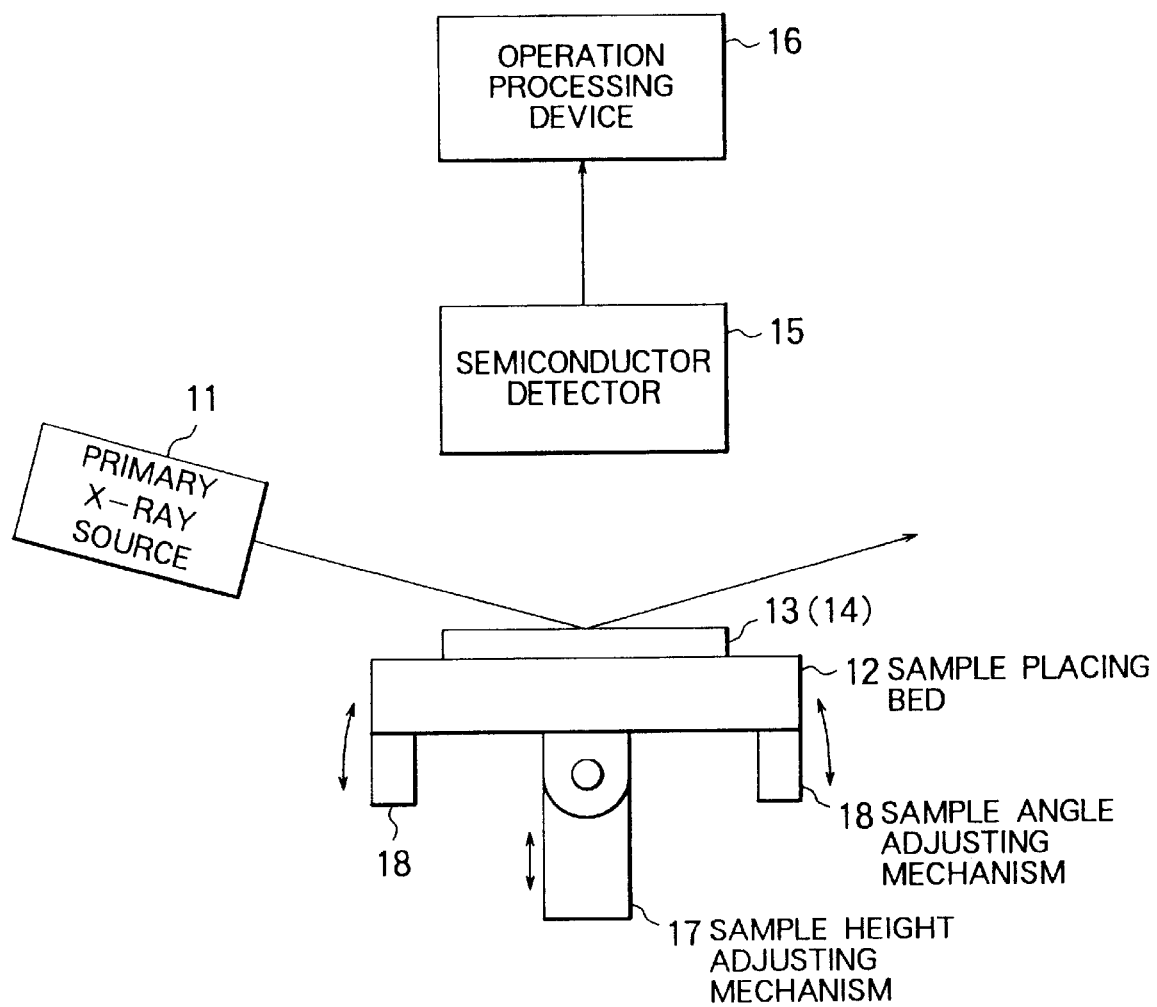
FIG. 1 is a schematic constitutional view illustrating an embodiment of the present invention.

FIG. 1 is a schematic constitutional view illustrating an outlined constitution of an apparatus for reflection X-ray fluorescence spectroscopy to which the present invention is applicable, in which 11 is a primary X-ray source constituted, for example, with an X-ray tubular bulb for emitting primary X-rays, and WL$\beta$ rays in the primary X-rays emitted from the primary X-ray source 11 are irradiated to a measured sample 13 or a standard sample 14 carried selectively as a measured sample on a sample placing bed 12.

The sample placing bed 12 has a sample height adjusting mechanism 17 for adjusting the height of the sample 13, 14, and a sample angle adjusting mechanism 18 for precisely adjusting an incident angle of the primary X-rays relative to the sample, in which the height of the sample placing bed 12 is adjusted vertically such that WL$\beta$ rays from the primary X-ray source 11 are irradiated to the center of the sample 13, 15 by the sample height adjusting mechanism 17 and, in this state, the incident angle smaller than the critical total reflection angle of the primary X-rays relative to the standard sample 14 (about 0.17°) is accurately changed and adjusted at a predetermined resolution power (for example, on 0.01° unit) successively, by the sample angle adjusting mechanism 18 thereby enabling to measure the characteristic X-ray spectra at a plurality of incident angles and enabling to measure the characteristic X-ray spectrum for the measured sample 13 by adjusting the incident angle of the primary X-rays to a specified angle.

Then, the characteristic X-ray spectrum emitted upon irradiation of the primary X-rays from the primary X-ray source 11 to the sample 13, 14 is detected by a semiconductor detector 15 disposed above and opposed to the sample placing bed 12, and a detection signal is subject to predetermined amplifying processing or the like and inputted to an operation processing device 16 for amplitude analysis thereby analyzing the characteristic X-ray spectrum.

The operation processing device 16 has a function of separating the measured characteristic X-ray spectrum into a characteristic X-ray intensity and a scattered X-ray intensity. By this function, the characteristic X-ray spectra measured by the incidence of the primary X-rays to the standard sample 14 at a plurality of incident angles can be separated into the characteristic X-ray intensity and the scattered X-ray intensity.

Further, the operation processing device 16 can input the quantity of the analyzed element on the standard sample 14 and has a function of determining a calibration coefficient by dividing the quantity with a previously determined characteristic X-ray intensity and a function of storing the calibration coefficient as a function of the previously determined scattered X-ray intensity.

Explanation will then be made to an example of a method for analyzing a measured sample having irregularities on the surface by using the apparatus.

In this case, a silicon wafer contaminated at a rear face with cobalt Co is used as the measured sample 13, while a silicon wafer having a substantially smooth surface, which is contaminated with an aqueous Co solution at a predetermined concentration by a spin coating method, is used as the standard sample 14 relative to the measured sample.

In this case, for calculating the quantity of Co on the surface of the standard sample, it is recovered by nitric acid and then quantitatively determined by using an induction coupling plasma mass spectrometer (ICP-MS). SPQ 8000A manufactured by Seiko Denshi Kogyo Co. is used as the induction coupling plasma mass spectrometer while the quantitative determination is indispensable to the preparation of a standard sample and should be practiced essentially before conducting total reflection X-ray spectroscopy, it is conducted after all measurement for the total reflection X-ray fluorescence spectroscopy have been conducted, this is a destructive analysis in view of the principle. Further, for demonstrating the validity of the fluorescence X-ray spectroscopy in the present invention, identical analysis was conducted also for the measured sample.

Figure 2:
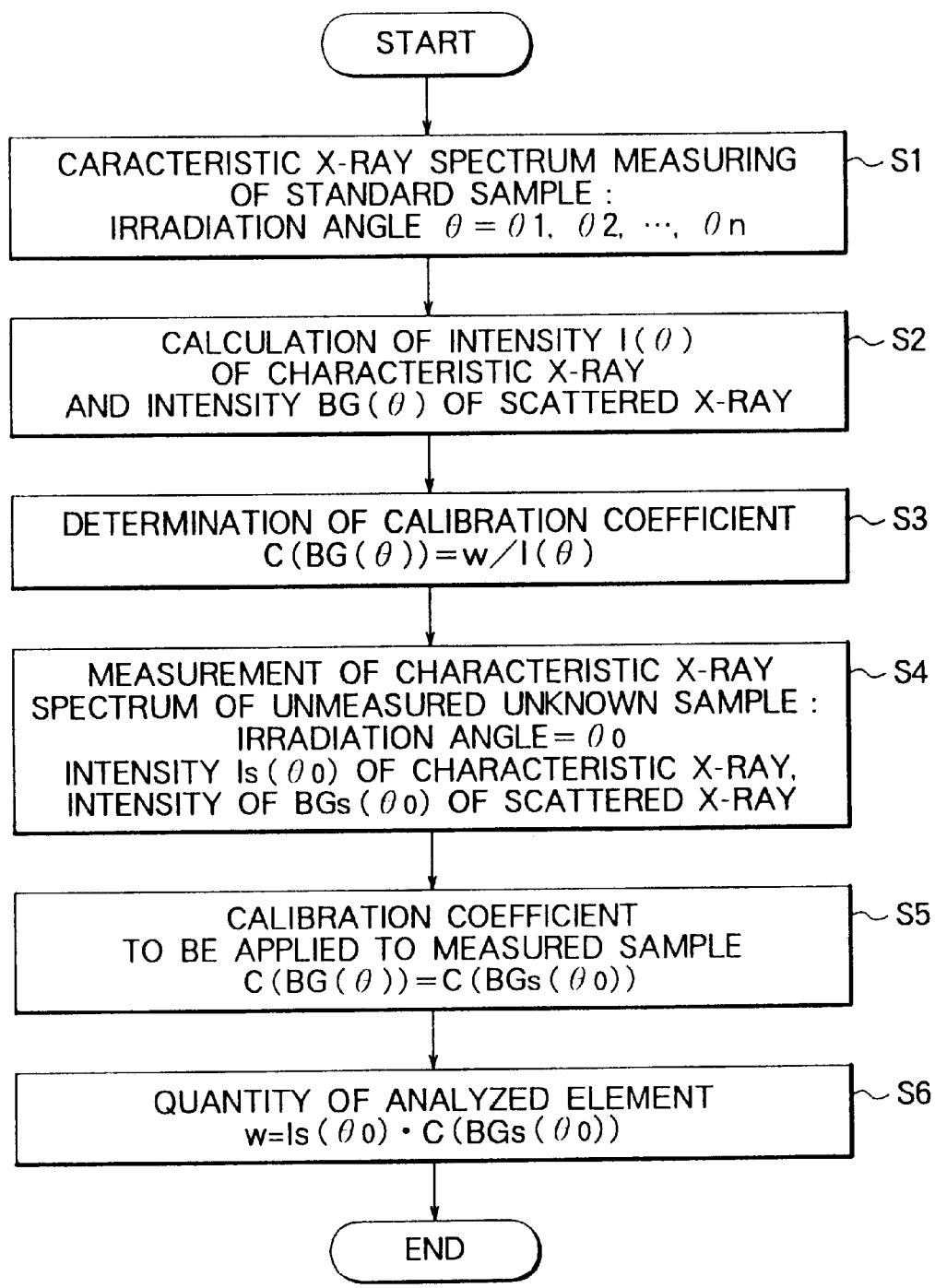
FIG. 2 is a flow chart illustrating an example of processing procedures in an operation processing device.

The total reflection X-ray fluorescent spectroscopy is conducted by using by adjusting the incident angle of the primary X-rays to a specified angle an apparatus by adjusting the incident angle of the primary X-rays to a specified angle of such a constitution and practicing the processing of a flow chart shown in FIG. 2 in the operation processing device 16.

At first, as a first step, the standard sample 14 described above is carried on the sample placing bed 12, the irradiation angle of the primary X-rays from the primary X-ray source 11 relative to the standard sample 14 is varied from 0.01° to 0.19° a step of 0.01° including a reference irradiation angle $\theta_0$ (0.05° a step of 0.01° in this state, and the characteristic X-ray spectrum at each of the steps is measured by the operation processing device (step S1). In the characteristic X-ray spectrum, a peak for CoK$\alpha$ rays appears as a characteristic X-ray peak for Co as the contaminant element and, at the same time, a background of scattered X-rays at a wavelength of the characteristic X-rays also appears.

Then, as a second step, an intensity $I(\theta)$ of CoKα rays and an intensity $BG(\theta)$ of scattered X-rays measured are separated for each of the measured characteristic X-ray spectra at each step by a curve fitting method as the spectroscopic method in the operation processing device 16 (step S2). The result of the operation is shown in Table 1 of the next page.

TABLE 1

| θ | I (θ) | BG (θ) |
|---|---|---|
| 0.01 | 0.0819 | 0.0060 |
| 0.02 | 0.2038 | 0.0074 |
| 0.03 | 0.3148 | 0.0150 |
| 0.04 | 0.5298 | 0.0270 |
| 0.05 | 0.8920 | 0.0233 |
| 0.06 | 1.1704 | 0.0369 |
| 0.07 | 1.5195 | 0.0463 |
| 0.08 | 1.8808 | 0.0651 |
| 0.09 | 2.4781 | 0.0789 |
| 0.10 | 3.0920 | 0.0869 |
| 0.11 | 3.4890 | 0.1333 |
| 0.12 | 4.3580 | 0.1281 |
| 0.13 | 5.2072 | 0.1584 |
| 0.14 | 5.8051 | 0.2253 |
| 0.15 | 6.8453 | 0.2176 |
| 0.16 | 7.2809 | 0.3016 |
| 0.17 | 8.0758 | 0.3956 |
| 0.18 | 8.7998 | 0.7408 |
| 0.19 | 9.1553 | 1.2249 |

Then, as a third step, a calibration coefficient $C(BG(\theta))$ illustrating a relation between the intensity $I(\theta)$ of CoKα rays and the quantity W of the analyzed element obtained in the second step is operated in accordance with the following equation (1) and determined as a function of an intensity $BG(\theta)$ of the scattered X-rays (step S3).

$$C(BG(\theta))=w/I(\theta) \quad (1)$$

In this case, the quantity w of the analyzed element in the standard sample 14 was $3.755 \times 10^{13}$ atom/cm² as a result of recovering Co on the surface of the standard sample by nitric acid after the end of the total reflection X-ray fluorescence spectroscopy and quantitatively determining by using an induction coupling plasma mass spectrometer (ICP-MS).

The result of the operation is shown in the following Table 2.

TABLE 2

| θ | Scattered X-ray Intensity BG (θ) | Calibration Coefficient C(BG(θ)) |
|---|---|---|
| 0.01 | 0.0060 | 45.86 |
| 0.02 | 0.0074 | 18.43 |
| 0.03 | 0.0150 | 11.92 |
| 0.04 | 0.0270 | 7.080 |
| 0.05 | 0.0233 | 4.210 |
| 0.06 | 0.0369 | 3.208 |
| 0.07 | 0.0463 | 2.470 |
| 0.08 | 0.0651 | 1.997 |
| 0.09 | 0.0789 | 1.515 |
| 0.10 | 0.0869 | 1.214 |
| 0.11 | 0.1333 | 1.076 |
| 0.12 | 0.1281 | 1.083 |
| 0.13 | 0.1584 | 0.721 |
| 0.14 | 0.2253 | 0.646 |
| 0.15 | 0.2176 | 0.548 |

TABLE 2-continued

| θ | Scattered X-ray Intensity BG (θ) | Calibration Coefficient C(BG(θ)) |
|---|---|---|
| 0.16 | 0.3016 | 0.515 |
| 0.17 | 0.3956 | 0.465 |
| 0.18 | 0.7408 | 0.426 |
| 0.19 | 1.2249 | 0.410 |

Figure 3:
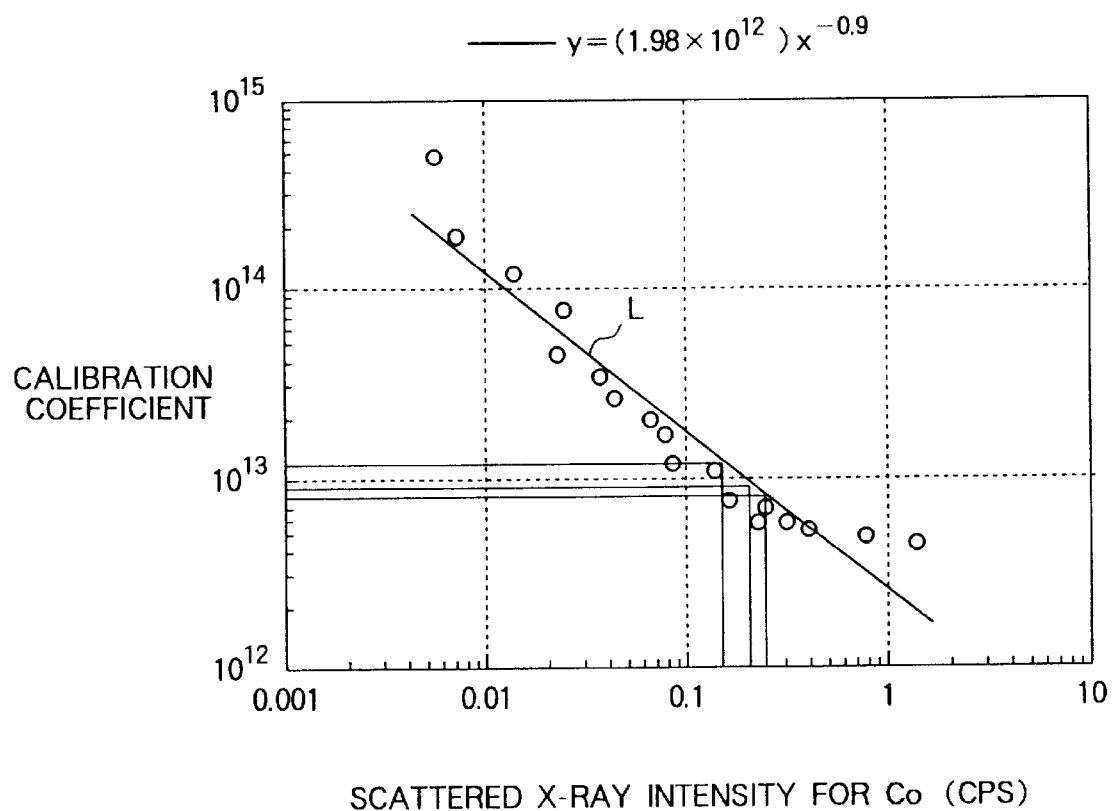
FIG. 3 is a characteristic diagram illustrating a relationship between a scattered X-ray intensity and a calibration coefficient for Co.

FIG. 3 shows a relation between the calibration coefficient $C(BG(\theta))$ and the scattered X-ray intensity $GB(\theta)$ using Table 2. FIG. 3 is convenient for obtaining a value of the calibration coefficient to be applied to each of the samples in actual measurement of measured samples.

In FIG. 3 shows the dependence of the calibration coefficient $C(GB(\theta))$ on the intensity of scattered X-rays $GB(\theta)$ by an exponentially approximated calibration line L and the approximated equation of the characteristic line L can be expressed by the following equation (2) and, by storing the approximated equation in a predetermined memory region of an incorporated memory, the calibration coefficient $C(BG(\theta))$ is calculated in accordance with the equation (2) in this embodiment.

$$C(BG(\theta))=1.99 \times 10^{12} \cdot BG(\theta)^{-0.9} \quad (2)$$

Then, as a fourth step, a measured sample 13 having irregularities on the surface is carried, instead of the standard sample 14, on the sample placing bed 12 of the apparatus for X-ray fluorescence spectroscopy, the primary X-ray source 11 is irradiated to the measured sample 13 at a reference irradiation angle $\theta_0$ (=0.05°), the characteristic X-ray spectrum in this case is measured, and the characteristic X-ray intensity $I_S(\theta_0)$ for Co and the scattered X-ray intensity $BG_S(\theta)$ at the wavelength are calculated by the curve fitting method in the same manner as for the standard sample (Step S4).

In this case, a rear face of a silicon wafer of the same lot as used for the standard sample 14 was used as the measured sample 13. Also for the measured sample 13, the amount of contamination was determined quantitatively by using the induction coupling plasma mass spectrometer and compared with the analytical value in the present invention.

Then, a calibration coefficient $C(BG_S(\theta_0))$ is determined by conducting operation for the equation (2) on the basis of the scattered X-intensity $BG_S(\theta_0)$ for the measured sample 13 (Step 5).

Then, as a fifth step, the quantity W for Co on the measured sample 13 is calculated in accordance with the following equation (3) on the basis of the determined calibration coefficient $C(BG_S(\theta_0))$ and the characteristic X-ray intensity $I_S(\theta_0)$ for the measured sample 13 determined in the step 4 (Step S6).

$$W=I_S(\theta_0) \times C(BG_S(\theta_0)) \quad (3)$$

In the processing in FIG. 2, processings at steps S1 and S2 correspond to the X-ray intensity measured means for standard sample, the processing at step S3 corresponds to the function memory means, the processing at step 4 corresponds to the X-ray intensity measuring means for the measured sample and the processing at step S5 corresponds to the calibration coefficient calculation means and the processing at step S6 corresponds to the calculation means for the quantity of element.

The following Table 3 collective shows the result for the processings in each of the steps described above on three measured samples and a result of recovering Co on the surface for each of the measured samples by nitric acid after the end of measurement of the total reflection X-ray spectroscopy and determining by the induction coupling plasma mass spectrometer (ICP-MS).

For the comparison, Table 3 also shows measured values by comparative examples not using the apparatus and the method of the present invention but by the calculation of simply multiplying the calibration coefficient determined by using a substantially smooth standard sample with the characteristic X-ray intensity in addition to the measuring values of the present invention.

TABLE 3

| Sample No. | Characteristic X-ray intensity for Co (cps) | Scattered X-ray intensity (CPS) | Calibration coefficient (atom/cm$^2$ CPS) | Measured value of the invention (atom/cm$^2$ CPS) | Measured value by ICP-MS (atom/cm$^2$ CPS) | Measured value of Comparative example (atom/cm$^2$ CPS) |
|---|---|---|---|---|---|---|
| 1 | 0.0136 | 0.147 | 1E + 13 | 1E + 11 | 2E + 11 | 5E + 11 |
| 2 | 0.0421 | 0.189 | 9E + 12 | 4E + 11 | 3E + 11 | 2E + 12 |
| 3 | 0.0408 | 0.220 | 7E + 12 | 3E + 11 | 5E + 11 | 2E + 11 |

As apparent from Table 3, the quantity W for the analyzed element Co calculated by multiplying the for the characteristic X-ray intensity ($I_S(\theta)$) for each of the measured samples 13 with the calibration coefficient $C(BG_S(\theta))$ is substantially identical with the measured value obtained by recovering Co from each of the measured samples 13 and determining by induction coupling plasma mass spectrometer (ICP-MS). On the contrary, for the measured values in comparative examples not relying on the present invention, there is a significant difference relative to the measured value determined by ICP-MS, which is remarkable in a sample with a marked degree of irregularities, that is, great scattered X-ray intensity.

As described above according to this invention, the total reflection X-ray fluorescence spectroscopy for the measured sample can be conducted easily by merely providing a standard sample 14 of a smooth surface without preparing a standard sample having identical irregularities with those of the measured sample 13.

In the embodiments described above, explanation has been made to a case of setting the reference irradiation angle $\theta_0$ relative to the measured sample 13 to 0.05°, but it is not restricted only thereto and it can be set to an optional value smaller than the critical total reflection angle.

Further, in the embodiment described above, explanation has been made to a case of disposing the angle adjusting mechanism 18 to the sample placing bed 12 and controlling the incident angle of the primary X-rays incident to the samples 13, 14, but it is not restricted only thereto and the incident angle of the primary X-rays relative to the sample 13, 14 may be controlled by disposing an angle adjusting mechanism for the primary X-ray source 11.

Further, in the embodiment described above, explanation has been made to a case of storing, into an incorporated memory, an approximate equation represented by the formula (2) of the characteristic line L approximating the relation between the scattered X-ray intensity $BG(\theta)$ for Co and the calibration coefficient $C(BG(\theta))$ and operating the calibration coefficient $C(BG(\theta))$ in accordance with the equation (2) on the basis of the scattered X-ray intensity $BG_S(\theta)$, but it is not restricted only thereto and it may be adapted such that a control map corresponding to the characteristic line L of FIG. 3 is previously stored in the incorporated memory, and the calibration curve $C(BG(\theta))$ may be determined referring to the control map on the basis of the of the scattered X-ray intensity $BG_S(\theta)$.

Furthermore, explanation has been made to a case that the standard sample is prepared of a material identical with that of the measured sample in the foregoing embodiment, but this is not restricted only thereto so long as it has a composition substantially identical with that of the measured sample having analyzed the element.

Furthermore, explanations has been made to the present invention in a case of conducting total reflection X-ray fluorescence spectroscopy for Co on the silicon wafer, but the present invention is not restricted only thereto but applicable to the total reflection X-ray fluorescence spectroscopy for any other optional analyzed element.

Industrial Applicability

As has been explained above, according to the method and the apparatus for total reflection X-ray fluorescence spectroscopy of the present invention, since an excellent effect capable of easily and accurately conducting analysis for the analyzed substance, without forming irregularities in accordance with the measured sample, or without operation of depositing a known quantity of analyzed sample and calibration, it can be utilized suitably to the total reflection X-ray fluorescent spectroscopy for measured samples having irregularities on the surfaces.

We claim:

1. An apparatus for total reflection X-ray fluorescence spectroscopy of irradiating primary X-rays to a measured sample at an angle near a critical total reflection angle, and measuring a characteristic X-ray spectrum emitted from the measured sample by the primary X-rays thereby analyzing an analyzed element on the measured sample, wherein the apparatus comprises an X-ray intensity measuring means for irradiating primary X-rays previously on a standard sample having substantially the same composition as that of a measured sample having a smooth surface at a plurality of irradiation angles near a total reflection angle, means for determining a characteristic X-ray intensity for an analyzed element and a scattered X-ray intensity at a wavelength of the characteristic X-rays for the analyzed element, a function memory means for determining a calibration coefficient indicative of a relation between the characteristic X-ray intensity determined by the X-ray intensity measuring means for the standard sample and a known quantity of the analyzed element on the basis of both of them as a function of the scattered X-ray intensity and storing the function, an X-ray intensity measuring means for measuring a characteristic X-ray spectrum when the primary X-rays are irradiated to the measured sample at an angle smaller than a critical total reflection angle and determining a characteristic X-ray intensity for the analyzed element appearing in the characteristic X-ray spectrum and a scattered X-ray intensity at a wavelength of the characteristic X-rays for the analyzed element, a calibration coefficient calculation means for determining a calibration coefficient by substituting the scattered X-ray intensity determined by the X-ray intensity measuring means for the measured sample as a scattered X-ray intensity of the function stored in the function memory means, and a calculation means for calibrating the characteristic X-ray intensity for the analyzed element determined by the calibration coefficient calculation means and calculating the quantity of the analyzed element.

2. An apparatus for total reflection X-ray fluorescence spectroscopy as defined in claim 1, wherein the function memory means stores the relation between the scattered X-ray intensity and the calibration coefficient as a functional equation.

3. An apparatus for total reflection X-ray fluorescence spectroscopy as defined in claim 1, wherein the function memory means stores the relation between the scattered X-ray intensity and the calibration coefficient as a control mat.

4. A method for total reflection X-ray fluorescence spectroscopy of irradiating primary X-rays to an analyzed substance on a measured sample at an angle near a critical total reflection angle, measuring a characteristic X-ray spectrum and a scattered X-ray spectrum emitted by the primary X-ray from the measured sample thereby analyzing the analyzed substance on the measured sample, comprising a first step of irradiating primary X-rays previously on a standard sample having substantially the same composition as that of a measured sample and having a smooth surface at a plurality of irradiation angles near a total reflection angle and measuring the characteristic X-ray spectrum, a second step of calculating the characteristic X-ray intensity for the analyzed element and the scattered X-ray intensity at the wavelength of the characteristic X-rays for the analyzed element by using the measured characteristic X-ray spectrum and determining a calibration coefficient indicative of a relationship between the calculated characteristic X-ray intensity and a known quantity of the analyzed element on the basis of both of them as a function of the scattered X-ray intensity, a third step of measuring the characteristic X-ray spectrum when primary X-rays are irradiated to a measured sample at an angle smaller than a critical total reflection angle and determining a characteristic X-ray intensity for the analyzed element appearing in the characteristic X-ray spectrum and a scattered X-ray intensity at a wavelength of the characteristic X-rays for the analyzed element, a fourth step of applying the scattered X-ray intensity for the analyzed element determined in the third step to the function of the calibration coefficient in the second step and determining a calibration coefficient to be applied to the measured sample and a fifth step of multiplying the characteristic X-ray intensity for the analyzed element determined in the third step with the calibration coefficient determined in the fourth step to calculate the quantity of the analyzed element.

* * * * *